United States Patent [19]

Bosies et al.

[11] Patent Number: 4,826,858

[45] Date of Patent: May 2, 1989

[54] N-SUBSTITUTED AZIRIDINE-2-CARBOXYLIC ACID DERIVATIVES, PROCESSES FOR THE PREPARATION THEREOF AND PHARMACEUTICAL COMPOSITIONS CONTAINING THEM

[75] Inventors: Elmar Bosies, Weinheim; Richard Endele, Wilhelmsfeld; Wulf Pahlke, Mannheim, all of Fed. Rep. of Germany

[73] Assignee: Boehringer Mannheim GmbH, Mannheim, Fed. Rep. of Germany

[21] Appl. No.: 125,353

[22] Filed: Nov. 25, 1987

Related U.S. Application Data

[63] Continuation-in-part of Ser. No. 804,156, Dec. 3, 1985, abandoned.

[30] Foreign Application Priority Data

Dec. 21, 1984 [DE] Fed. Rep. of Germany ....... 3446713

[51] Int. Cl.$^4$ .................... C07D 401/06; A61K 31/44
[52] U.S. Cl. ..................................... 514/340; 546/275
[58] Field of Search ......................... 546/275; 514/340

[56] References Cited

U.S. PATENT DOCUMENTS 4,321,194  3/1982  Bosies et al. ......................... 514/183
4,409,236  10/1983  Bosies et al. ......................... 514/444
4,410,532  10/1983  Bosies et al. ......................... 514/256

Primary Examiner—Alan L. Rotman
Attorney, Agent, or Firm—Felfe & Lynch

[57] ABSTRACT

The present invention is concerned with N- substituted aziridine-2-carboxylic acid derivatives, with pharmaceutical compositions containing these compounds and their immuno-stimulating and immuno-modulating activities.

8 Claims, No Drawings

N-SUBSTITUTED AZIRIDINE-2-CARBOXYLIC ACID DERIVATIVES, PROCESSES FOR THE PREPARATION THEREOF AND PHARMACEUTICAL COMPOSITIONS CONTAINING THEM

This application is a continuation-in-part of Ser. No. 804,156, filed Dec. 3, 1985, and now abandoned.

U.S. Pat. No. 4,410,532 issued Oct. 18, 1983 describes N-alkylated aziridine-2-carboxylic acid derivatives with immune-stimulating action, including 2-cyano-1-[(2-methoxy-6-methyl-3-pyridinyl)-methyl]-aziridine (ciamexone).

We have now found that other N-pyridinylmethyl-aziridine-carboxylic acid derivatives, some of which are metabolites of the above-mentioned compound, exhibit a remarkable immune-suppressing action, so that they can be used as immune-modulators. Immunomodulators cause on the one hand an increase of the immune reaction and on the other hand a suppression, however, it is extremely difficult to prove this modulation (Enzyklopeaedia of Chem. Tech. 13, 171 pp, 1981-Kirk-Othmer 3rd ed., John Wiley and Son, N.Y.). As such said compounds are effective in treating conditions where elevated levels of antibody production or monocyte/lymphocyte activity as a result of the hyperreactivity of the immunoregulatory network are closely associated with the development of autoimmune diseases, including rheumatoid arthritis [Mellbye, O. J. and Natvig, J. B. Clin. Exp. Immunol., 8, 889 (1971)], multiple sclerosis [Tourtellotte, W. W. and Parker, J. A., Science, 154, 1044 (1966)], systemic lupus erythematosis [Abdou, N. I., et al., Clin. Immunol. Immunopath., 6, 192 (1976)], thyroiditis [Witebsky, E., et al., J. Immunol., 103, 708 (1969)], mixed connective tissue disease [Sharp, G. C., et al., Am. J. Med., 52, 148 (1972)], dermato/polymyositis [Venables, P. J. W., et al., Ann. Rheum. Dis., 40, 217 (1981)], insulin-dependent diabetes [Charles, M. A., et al., J. Immunol., 130, 1189 (1983)] and in patients undergoing organ transplantation.

Thus, according to the present invention, there are provided aziridine-2-carboxylic acid derivatives of the general formula:

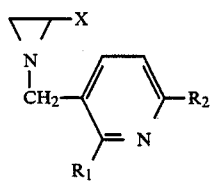

(I)

wherein X is a nitrile, carboxyl, alkoxycarbonyl or carbamoyl radical, $R_1$ is a hydroxyl group or an alkoxy radical and $R_2$ is a hydroxymethyl, carboxyl, alkoxycarbonyl, formyl or carbamoyl radical, and the salts and N-oxides thereof, these compounds having an immune-modulating action.

The present invention also includes all the stereoisomers which exist, for example, because of the presence of asymmetric carbon atoms, separation of the stereoisomeric forms being carried out by known processes.

An alkoxy radical is to be understood to mean a radical containing 1 to 4 carbon atoms, the methoxy and ethoxy radicals being preferred. The alkoxycarbonyl radicals X and $R_2$ are radicals containing 2 to 5 carbon atoms, the methoxycarbonyl and ethoxycarbonyl radicals being preferred.

The compounds of general formula (I) can be preferred by known processes and preferably by (a) reacting a compound of the general formula:

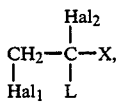

(II)

in which X has the above-given meaning, $Hal_1$ and $Hal_2$ are chlorine or bromine atoms and L is a hydrogen atom or in which $Hal_1$ and L together represent a valency bond, with an amine of the general formula:

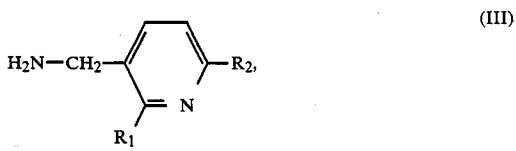

(III)

or with an N-oxide thereof, in which $R_1$ and $R_2$ have the above-given meanings; or (b) treating a compound of the general formula:

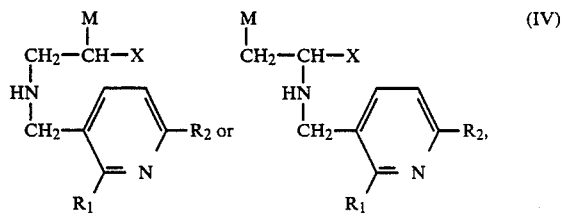

(IV)

or a salt or N-oxide thereof, in which X, $R_1$ and $R_2$ have the above-given meanings and M is a chlorine or bromine atom or a group A-Z, A being an oxygen or sulphur atom and Z a hydrogen atom or, together with oxygen or sulphur, a grouping which is easy to eliminate, with a reagent splitting off M-H; or (c) reacting a compound of the general formula:

(V)

in which X has the above-given meaning, with a compound of the general formula:

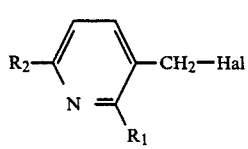

or an N-oxide thereof, in which $R_1$ and $R_2$ have the above-given meanings and Hal is a chlorine, bromine or iodine atom; or (d) reacting an azide of the general formula:

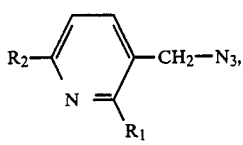 (VII)

or an N-oxide thereof, in which $R_1$ and $R_2$ have the above-given meanings, with a compound of the general formula:

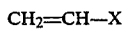 (VIII)

in which X has the above-given meaning, to give a compound of general formula (I), whereby, as intermediate step, there can be formed a triazoline of the general formula:

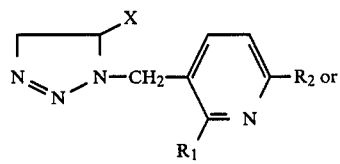 (IX)

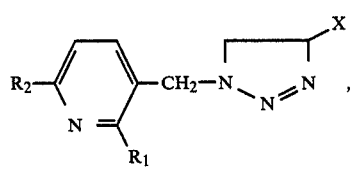

or an N-oxide thereof, in which $R_1$, $R_2$ and X have the above-given meanings, which, by thermolysis or photolysis, can be converted into a compound of the general formula (I) with splitting off of nitrogen; or (e) reacting an epoxide of the general formula:

in which X has the above-given meaning, with an amine of general formula (III) or an N-oxide thereof; or (f) subjecting an oxazolidinone of the general formula:

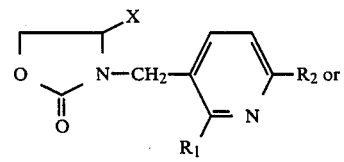 (XI)

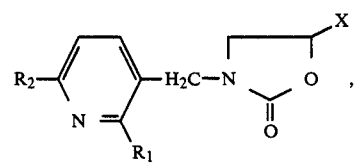

or an N-oxide thereof, in which $R_1$, $R_2$ and X have the above-given meanings, to a thermolysis; or (g) treating a compound of the general formula:

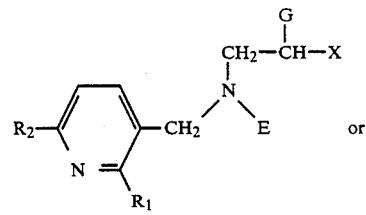 (XII)

or

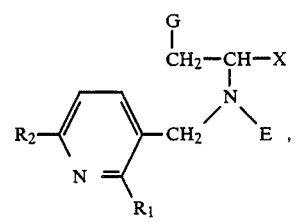

or an N-oxide thereof, in which $R_1$, $R_2$ and X have the above-given meanings, G is a hydrogen atom or Hal and E is Hal or a trialkylamino radical or an arylsulphonic acid ester residue, Hal being a chlorine or bromine atom, with a reagent splitting off E-G, whereafter, if desired, a compound obtained of general formula (I) is converted into another compound of general formula (I) and, if desired, a compound of general formula (I) is converted into a pharmacologically acceptable salt.

Process (a) for the preparation of the aziridine derivatives of general formula (I) is known from the literature (see, for example, Gundermann et al., Chem. Ber., 105, 312 (1972) and Wagner-Jauregg, Helv. Chim. Acta, 44, 1237 (1961)). An inert solvent, for example diethyl ether, dioxan, benzene, toluene or the like, is hereby preferably employed but a lower alcohol, for example methanol or ethanol or the like, can also be used. The reaction temperature is from 0° to 80° C., it being preferred to work at ambient temperature. The reaction time can be from 3 hours to 10 days.

In the case of process (b), the reagent splitting off M-H is a base and preferably a tertiary amine, for example triethylamine, triethanolamine, dicyclohexylethylamine or the like. An inert solvent, such as diethyl ether, dioxan, benzene or toluene, can hereby be used but an alcohol, such as methanol or ethanol is also suitable. Furthermore, in some cases, use is preferably made of an alcoholate, such as sodium methylate or sodium ethylate, in the corresponding alcohol. When the group A-Z is a hydroxyl group, the agent splitting off water is preferably triphenyl phosphine in the presence of carbon tetrachloride and triethylamine, methylene chloride or chloroform preferably then being used as solvent. However, the splitting off of water can also take place with sulphuric acid. The reaction time is from 3 to 24 hours.

The alkylation reaction in the case of process (c) is preferably carried out in water, an alcohol, such as methanol or ethanol, or in an alcohol/water mixture in the presence of a base. Besides organic bases, use can also be made of inorganic based, for example alkali metal carbonates or alkali metal bicarbonates, as acid acceptors. As a rule, the reaction is carried out at a temperature of from 20° to 60° C. In order to speed up the reaction, a phase transfer catalyst, for example triethylbenzylammonium chloride, can be added.

The thermolysis of the triazolines in the case of process (d) is carried out at 80° to 150° C. and preferably at 100° to 120° C. The thermolysis can be carried out without the use of a solvent, the resultant aziridine derivative being purified by distillation or recrystallization. However, use can also be made of solvents, in which case an inert solvent, for example benzene, toluene or xylene, has proved to be especially useful. Photolyses are usually carried out at ambient temperature in solution, in which case benzene, toluene or also acetonitrile are preferably used. The photolyses can be carried out with or without the use of sensitisers, for example benzoquinone or acetophenone (see, for example, J.A.C.S., 90, 988 (1968)).

In the case of process (e), an epoxide of general formula (X) is reacted with an amine of general formula (III) or with an N-oxide thereof, the aminoalcohol thereby formed being dehydrated to give an aziridine derivative of general formula (I) in the manner described in process (b).

Oxazolidinones of general formula (XI) are, as a rule, thermolysed without the use of a solvent in the presence of a base, for example triethanolamine or dicyclohexylethylamine. The thermolysis temperature is from 170° to 250° C.

In the case of process (g), the reagent splitting off E-G, when G is a hydrogen atom, is preferably an alcoholate, such as alkali metal methylate or alkali metal ethylate, in the corresponding alcohol. However, use can also be made of a tertiary amine, such as triethylamine, thriethanolamine or dicyclohexylethylamine in a solvent, such as methanol, ethanol, benzene, toluene, diethyl ether or dioxan. When G and E are Hal, the splitting off can be carried out with the use of conventional dehalogenation agents and preferably of zinc or sodium.

The subsequent conversion of a compound of general formula (I) into another compound of general formula (I) can take place by the conversion of the substituents X and $R_2$. Thus, for example, a compound in which X or $R_2$ is an alkoxycarbonyl radical can be converted by reaction with ammonia into a compound in which X or $R_2$ is a carbonyl radical and, when X is a carbamoyl radical, this can, in turn, be converted by means of a dehydration agent into a compound in which X is a nitrile group.

Compounds of general formula (I), in which X is an alkoxycarbonyl or carbamoyl radical, can, therefore, also be used as intermediates for the preparation of compounds of general formula (I), in which X is a nitrile group.

Compounds of general formula (I), in which $R_2$ is a hydroxymethyl radical, can be prepared by the reduction of a corresponding compound in which $R_2$ is a carboxyl, formyl or alkoxycarbonyl radical.

Compounds of general formula (I), in which $R_2$ is a carboxyl group, can be prepared by the oxidation of compounds of general formula (I), in which $R_2$ is a hydroxymethyl or formyl radical, or by saponification of compounds of general formula (I), in which $R_2$ is an alkoxycarbonyl or carbamoyl radical.

Compounds of general formula (I), in which $R_2$ is an alkoxycarbonyl, formyl or carbamoyl radical, can, therefore, also be used as intermediates for the preparation of compounds of general formula (I), in which $R_2$ is a hydroxymethyl or carboxyl radical.

The subsequent conversion of compounds of general formula (I) into other compounds of general formula (I) can, on the other hand, also be carried out by conversion into the corresponding N-oxides or by reduction of the N-oxides to the corresponding nitrogen bases. The oxidation of the N-oxides takes place according to methods known from the literature and preferably by reaction with a peroxide, for example hydrogen peroxide, acetic acid thereby usually being employed as solvent. The reduction of an N-oxide is usually carried out by hydrogenation using Raney nickel as catalyst. As solvent, it is preferable to use a lower alcohol, such as methanol or ethanol.

The conversion of an ester into an amide grouping can be carried out with gaseous ammonia in an organic solvent, preferably methanol or ethanol, or with aqueous ammonia at 0° to +25° C. The desired amide precipitates out or is isolated from the reaction mixture, for example by column chromatography.

For the conversion of a carbamoyl group into a nitrile group, there are used dehydration agents known from the literature, a mixture of triphenyl phosphine, carbon tetrachloride and triethylamine preferably being used. The solvent used is preferably a halogenated hydrocarbon, for example, methylene chloride or chloroform, but acetonitrile can also be used.

The conversion of compounds of general formula (I) with an alkoxycarbonyl, carbamoyl or cyano group into a carboxyl compound usually takes place by saponification by processes known from the literature.

The conversion of an alkoxycarbonyl, formyl or carboxyl group into a hydroxymethyl group is preferably carried out with a borohydride, in which case the carboxyl group can possibly be previously activated, for example, by reaction to give a mixed anhydride. Use can be made, for example, of lithium borohydride, sodium borohydride/lithium chloride, sodium borohydride in polyethylene glycol, sodium borohydride/aluminium chloride or borane/tetrahydrofuran. As solvents, there are preferably used lower alcohols, such as methanol or ethanol, tetrahydrofuran, diethylene glycol dimethyl ether or polyethylene glycol. The reduction is carried out at a temperature of from 0° to 60° C. and preferably of from 20° to 30° C.

The oxidation of a hydroxymethyl or formyl radical into a carboxyl group can be carried out with conventional oxidation agents, for example potassium permanganate, tetrabutyl ammonium permanganate, bis-(tetrabutylammonium) dichromate, nickel peroxide or pyridinium dichromate. As solvent, there is hereby used, depending upon the oxidation agent, water, a halogenated hydrocarbon, diethyl ether or dimethylformamide, the reactions being carried out at a temperature of from 20° to 100° C.

For the preparation of pharmaceutical compositions with an immune-modulating action, the compounds of general formula (I) are mixed in known manner with appropriate pharmaceutical carrier substances and formed, for example, into tablets or dragees or, with the addition of corresponding adjuvants, suspended or dissolved in water or an oil, for example, olive oil, and filled into hard gelatine capsules.

Since the active material is acid labile, the composition is provided with a coating which is first soluble in the alkaline small-intestinal medium or an appropriate carrier material, for example a higher fatty acid or carboxymethylcellulose, is admixed therewith. Solid carrier materials include, for example, starch, lactose, mannitol, methyl cellulose, talc, high dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

As injection medium, water is preferably used which contains the additives usual in the case of injection solutions, such as stabilising agents, solubilising agents or weakly alkaline buffers. Such additives include, for example, dimethyl sulphoxide, dimethylformamide, N-methylpyrrolidone, phosphate and carbonate buffers, ethanol, complex formers (such as ethylenediamine-tetraacetic acid and the non-toxic salts thereof) and high molecular weight polymers (such as liquid polyethylene oxide) for viscosity regulation.

For combating diseases which can be treated by immune modulators, the pharmacologically active compounds of general formula (I) are employed in individual doses of 1 to 600 and preferably of 50 to 500 mg, whereby these individual doses, according to need, can be administered one or more times per day.

Preferred according to the present invention, apart from the compounds mentioned in the Examples, are the following compounds which can also be used for the preparation of pharmaceutical compositions with an immune-modulating action:

1-[(6-hydroxymethyl-2-hydroxy-3-pyridinyl)-methyl]-aziridine-2-carbonitrile

5-[(2-cyano-1-aziridinyl)-methyl]-6-hydroxypyridine-2-carboxylic acid methyl 5-[(2-cyano-1-aziridinyl)-methyl]-6-hydroxypyridine-2-carboxylate 5-[(2-cyano-1-aziridinyl)-methyl]-6-methoxypyridine-2-carboxamide 5-[(2-cyano-1-aziridinyl)-methyl]-6-hydroxypyridine-2-carboxamide 5-[(2-carboxy-1-aziridinyl)-methyl]-6-methoxypyridine-2-carboxylic acid 5-[(2-carboxy-1-aziridinyl)-methyl]-6-hydroxypyridine-2-carboxylic acid 1-[(6-hydroxymethyl-2-methoxy-3-pyridinyl)-methyl]-aziridine-2-carboxylic acid 1-[(6-hydroxymethyl-2-hydroxy-3-pyridinyl)-methyl]-aziridine-2-carboxylic acid 5-[(2-carboxy-1-aziridinyl)-methyl]-6-methoxypyridine-2-carboxamide 5-[(2-carboxy-1-aziridinyl)-methyl]-6-hydroxypyridine-2-carboxamide 5-[(2-ethoxycarbonyl-1-aziridinyl)-methyl]-6-methoxypyridine-2-carboxylic acid 5-[(2-ethoxycarbonyl-1-aziridinyl)-methyl]-6-hydroxypyridine-2-carboxylic acid 1-[(2-methoxy-6-methoxycarbonyl-3-pyridinyl)-methyl]-aziridine-2-carboxylic acid 1-[(2-hydroxy-6-methoxycarbonyl-3-pyridinyl)-methyl]-aziridine-2-carboxylic acid ethyl 1-[(2-methoxy-6-methoxycarbonyl-3-pyridinyl)-methyl-aziridine-2-carboxylate ethyl 1-[(2-hydroxy-6-methoxycarbonyl-3-pyridinyl)-methyl]-aziridine-2-carboxylate 5-[(2-ethoxycarbonyl-1-aziridinyl)-methyl]-6-methoxypyridine-2-carboxamide 5-[(2-ethoxycarbonyl-1-aziridinyl)-methyl]-6-hydroxypyridine-2-carboxyamide ethyl 1-[(6-hydroxymethyl-2-methoxy-3-pyridinyl)-methyl]-aziridine-2-carboxylate ethyl 1-[(2-hydroxy-6-hydroxymethyl-3-pyridinyl)-methyl]-aziridine-2-carboxylate 1-[(6-carboxy-2-methoxy-3-pyridinyl)-methyl]-aziridine-2-carboxamide 1-[(6-carboxy-2-hydroxy-3-pyridinyl)-methyl]-aziridine-2carboxamide 1-[(6-hydroxymethyl-2-methoxy-3-pyridinyl)-methyl]-aziridine-2-carboxamide 1-[(2-hydroxy-6-hydroxymethyl-3-pyridinyl)-methyl]-aziridine-2-carboxamide 1-[(2-methoxy-6-methoxycarbonyl-3-pyridinyl)-methyl]-aziridine-2-carboxamide 1-[(2-hydroxy-6-methoxycarbonyl-3-pyridinyl)-methyl]-aziridine-2-carboxamide 5-[(2-carboxamido-1aziridinyl)-methyl]-6-methoxypyridine-2-carboxamide 5-[(2-carboxamido-1-aziridinyl)-methyl]-6-hydroxypyridine-2-carboxamide 5-[(2-cyano-1-aziridinyl)-methyl]-6-methoxypyridine-N-oxide-2-carboxylic acid 5-[(2-carboxamido-1-aziridinyl)-methyl]-6-methoxypyridine-N-oxide-2-carboxylic acid 5-[(2-carboxamido-1-aziridinyl)-methyl]-6-hydroxypyridine-N-oxide-2-carboxylic acid The following Examples are given for the purpose of illustrating the present invention and some of the numerous process variants which can be used for the synthesis of the compounds according to the present invention.

The structures of all of the compounds described in the following Examples have been verified by microcombustion analyses, NMR and mass spectra.

EXAMPLE 1

5-[(2-Cyano-1-aziridinyl)-methyl]-6-methoxypyridine-2-carboxylic acid (sodium salt)

2.33 g. (44 mmol) acrylonitrile are diluted with 1 ml. diethyl ether and, while stirring and illuminating, 7.05 g. (44 mmol) bromine are added dropwise thereto. The mixture is occasionally cooled in order to ensure that the internal temperature does not exceed 40° C. Stirring is continued for a further 5 minutes, the reaction mixture is diluted with 60 ml. methanol and a solution of 6.55 g. (44 mmol) triethanolamine in 60 ml. methanol is added dropwise thereto. After a further hour, there are simultaneously added dropwise thereto a solution of 6.55 g. (44 mmol) triethanolamine in 60 ml. methanol and a solution of 8 g. (44 mmol) 5-aminomethyl-6-methoxypyridine-2-carboxylic acid (m.p. 269°–270° C. (decomp.)) in 1 liter methanol/200 ml. water. The solution is left to stand for 24 hours, then evaporated substantially on a rotary evaporator and the aqueous solution adjusted with 2N hydrochloric acid to a pH of 4.5, followed by extracting continuously for 2 days with methylene chloride. The methylene chloride phase is then dried and evaporated to give 4.8 g. of an oil which is dissolved in 50 ml. ethanol. While cooling, the solution is mixed with a solution of 440 mg. sodium in 15 ml. ethanol. The sodium salt of 5-[(2-cyano-1-aziridinyl)-methyl]-6-methoxypyridine-2-carboxylic acid precipitates out and, after the addition of 100 ml. isopropanol, it is filtered off with suction, dried and washed with diethyl ether to give 3.7 g. (33% of theory) of the desired compound; m.p. 230°–232° C.

From the methylene chloride extracts, after stripping off the methylene chloride and taking up the oily residue in a little isopropanol, by adding diethyl ether there can be isolated 5-[(2-cyano-1-aziridinyl)-methyl]-6-methoxypyridine-2-carboxylic acid; m.p. 96°–97° C.

The 5-aminomethyl-6-methoxypyridine-2-carboxylic acid used as starting material can be prepared as follows:

3-Cyano-2-methoxy-6-methylpyridine is oxidised with potassium permanganate in aqueous solution to give 5-cyano-6-methoxypyridine-2-carboxylic acid (m.p. 235°-237° C.), subsequent hydrogenation of which on palladium/charcoal in isopropanol/water/hydrochloric acid gives the desired compound.

In an analogous way, by reacting 2-bromoacrylonitrile, obtained by the bromination of acrylonitrile and splitting off of hydrogen bromide, with methyl 5-aminomethyl-6-methoxypyridine-2-carboxylate (m.p. of the hydrochloride: 224°-226° C.), there is obtained methyl 5-[(2-cyano-1-aziridinyl)-methyl]-6-methoxypyridine-2-carboxylate; m.p. 156°-158° C. (recrystallised from isopropanol); yield 57% of theory.

The methyl 5-aminomethyl-6-methoxypyridine-2-carboxylate used as starting material is prepared in the following way:

5-Cyano-6-methoxypyridine-2-carboxylic acid (see above) is reacted in methanol with the help of trimethylchlorosilane to give methyl 5-cyano-6-methoxypyridine-2-carboxylate (m.p. 125°-125° C.). Subsequent hydrogenation in methanol on palladium/charcoal in the presence of hydrochloride acid gives the desired aminomethyl compound (m.p. of the hydrochloride: 224°-226° C.). By the addition of a few drops of triethanolamine, the hydrogenation solution is brought to a pH of 7 and used directly for the following reaction.

EXAMPLE 2

1-[(6-Hydroxymethyl-2-methoxy-3-pyridinyl)-methyl]-2-aziridine-carbonitrile 247 mg. (1 mmol) methyl 5-[(2-cyano-1-aziridinyl)-methyl]-6-methoxypyridine-2-carboxylate (see Example 1) are dissolved in 10 ml. of anhydrous tetrahydrofuran and the solution is mixed with 74 mg. (2 mmol) sodium borohydride and 84 mg. (2 mmol) lithium chloride. After stirring for 12 hours at ambient temperature, the same amounts of sodium borohydride and lithium chloride are again added and, after a further 12 hours, the reaction mixture is mixed with 5 ml. water, evaporated and the residue taken up in ethanol and filtered. The filtrate is evaporated, the residue is taken up in acetone, filtered and evaporated. The residue is purified over a silica gel column (elution agent: acetone/toluene 1:3 v/v) (Rf value about 0.3) to give 120 mg. (55% of theory) of the desired product; m.p. 68°-70° C.

EXAMPLE 3

5-[(2-Cyano-1-aziridinyl)-methyl]-6-ethoxypyridine-2-carboxylate acid

In a manner analogous to that described in Example 1, by reacting 2-bromoacrylonitrile, obtained by brominating acrylonitrile and splitting off hydrogen bromide, with 5-aminomethyl-6-ethoxypyridine-2-carboxylic acid (m.p. 226°-228° C.), there is obtained 5-[(2-cyano-1-aziridinyl)-methyl]-6-ethoxypyridine-2-carboxylic acid in a yield of 35% of theory; m.p. 108°-111° C.

The 5-aminomethyl-6-ethoxypyridine-2-carboxylic acid used as starting material is prepared in the following way:

2-Chloro-6-methylpyridine-2-carbonitrile is reacted with sodium ethylate in ethanol to give 2-ethoxy-6-methylpyridine-3-carbonitrile (m.p. 90°-92° C.) and subsequently oxidised with potassium permanganate to give 5-cyano-6-ethoxypyridine-2-carboxylic acid (m.p. 185°-190° C.). By catalytic hydrogenation on palladium/charcoal, there is then obtained 5-aminomethyl-6-ethoxypyridine-2-carboxylic acid.

EXAMPLE 4

5-[(2-Cyano-1-aziridinyl)-methyl]-6-methoxypyridine-2-carboxyaldehyde 2.4 g. of the compound 1-[(6-Hydroxymethyl-2-methoxy-3-pyridinyl)-methyl]-2-aziridine-carbonitrile, as described in Example 2, are dissolved in 80 ml of methylene chloride and 6 g. of activated manganese dioxide are added thereto. The solution is stirred for 24 hrs. at room temperature, then the same amount of manganese dioxide is added thereto again and stirring is continued for further 24 hrs. at room temperature. The solution is filtered by suction, the filtrate evaporated substantially and the residue purified over a silica gel (elution agent: dioxane/ligroine 1:3 v/v). The fractions containing the desired compound are concentrated and the residue is recrystallized from toluene in a yield of 1.4 g. (59% of theory); m.p. 104°-105° C.

The following experiments prove the immunomodulating effect of the compounds of Examples 1 and 2. In the first part, the effect of ciamexone is compared with cyclosporin, which is well known for its immunesuppressing action. The data show, that the action of ciamexone is comparable to that of cyclosporin, i.e. ciamexone acts as immune-suppressive agent. The second part, shows results with compounds of Examples 1 and 2.

EXPERIMENTS

Effects of ciamexone on local Graft-versus-Host (GvH) and Host-versus-Graft (HvG) reactions in mice (1) Ciamexone was shown in the test model described below to act as immunsuppressive pharmaceutical compound by comparison with the well known action of cyclosporin.

Local GvH reactions were induced in (C57B1/6×Balb/c) $F_1$ hybrid mice by injection of $5\times10^6$ parental (Balb/c) spleen cells into the food pad of one hind leg. The same number of $F_1$ spleen cells were injected into the control foot pad on the contralateral side. For the Host-versus-Graft reaction $5\times10^6$ spleen cells of (Balb/c×C57B1/6) $F_1$ hybrid mice were injected into the foot pad of parental mice (Balb/c). The same number of Balb/c spleen cells were injected into the contralateral food pad (control). The extent of the ensuing GvH or HvG reaction was measured using a popliteal lymph node assay. On day 5 (GvH), or 3 (HvG) after cell injection the popliteal lymph nodes were removed and weighed. The weight increase of the node on the experimental side over the weight of the control side was a measure for the GvH/HvG reaction. The animals were treated orally with clamexone, or ciclosporin, at daily doses of 0.1–100 mg/kg. the treatment period was from the day of cell injection (day 0-time 0) to day +4 (GvH) or +2 (HvG).

TABLE 1

| Compound | Dose mg/kg | Δ Lymph node weight (mg × $10^{-1}$) | | | |
|---|---|---|---|---|---|
| | | GvH | | HvG | |
| | | $\bar{x}$ | $S_{\bar{x}}$ | $\bar{x}$ | $S_{\bar{x}}$ |
| Control | PBS | 45.2 | 8.3 | 35.5 | 10.3 |
| Ciamexone | 0.1 | 36.3 | 6.1 | 35.5 | 4.8 |
| | 1.0 | 25.7 | 10.5 | 21.5 | 4.8 |

TABLE 1-continued

| Compound | Dose mg/kg | Δ Lymph node weight (mg × $10^{-1}$) | | | |
|---|---|---|---|---|---|
| | | GvH | | HvG | |
| | | $\bar{x}$ | $S_{\bar{x}}$ | $\bar{x}$ | $S_{\bar{x}}$ |
| | 10.0 | 11.3* | 4.1 | 12.7* | 3.1 |
| | 100.0 | 3.5* | 1.9 | 7.5* | 3.7 |
| Control | Olive Oil | 36.3 | 8.5 | 43.3 | 9.4 |
| Cyclosporin | 0.1 | 35.7 | 10.8 | 36.2 | 6.0 |
| | 1.0 | 17.7* | 4.2 | 26.7* | 11.4 |
| | 10.0 | 8.5* | 3.8 | 10.7* | 5.7 |
| | 100.0 | 2.3* | 1.6 | 2.5* | 1.9 |

*p ≦ 0.05 (student's t-test)

As shown in the example of a representative experiment, ciamexone significantly suppressed the GvH as well as the HvG reaction tested in a comparable way as ciclosporin inhibits these reactions.

(2) Under comparable experimental conditions, 2-Cyano-1[(2-methoxy-6-corboxypyridine-3-yl)-methyl]-aziridine, Ex. 1 and 2-Cyano-1[(2-methoxy-6-hydroxymethylpyridine-3-yl)-methyl]-aziridine, Ex. 2 were investigated according to their immunsuppressive action in relationship to ciamexone. The daily doses varied from 0.1–10 mg/kg.

TABLE 2

| Compound | Dose mg/kg | Lymph node weight (mg × $10^{-1}$) | | | | | |
|---|---|---|---|---|---|---|---|
| | | $\bar{x}$ | $S_{\bar{x}}$ | $\bar{x}$ | $S_{\bar{x}}$ | $\bar{x}$ | $S_{\bar{x}}$ |
| | | syngenic | | allogenic | | Δ | |
| Control | | 9.9 | 0.3 | 42.6 | 1.9 | 32.7 | 1.8 |
| Ciamexone | 0.01 | 10.9 | 0.8 | 38.9 | 3.5 | 28.0 | 3.3 |
| | 0.1 | 9.0 | 0.7 | 26.4 | 2.3 | 17.4* | 2.1 |
| | 1.0 | 9.9 | 0.4 | 23.6 | 1.0 | 13.7* | 1.2 |
| | 10.0 | 9.9 | 0.3 | 14.1 | 0.6 | 4.2* | 0.6 |
| 2-Cyano-1-[(2-methoxy-6-carboxypyridine-3-yl)-methyl]-aziridine | 0.01 | 9.5 | 0.7 | 27.2 | 1.1 | 17.7* | 1.3 |
| | 0.1 | 9.2 | 0.4 | 22.2 | 1.1 | 13.0* | 1.1 |
| | 1.0 | 10.2 | 0.6 | 24.2 | 1.3 | 14.0* | 1.2 |
| | 10.0 | 10.2 | 0.5 | 21.6 | 0.9 | 11.4* | 0.6 |
| 2-Cyano-1-[(2-methoxy-6-hydroxymethyl-pyridine-3-yl)-methyl]-aziridine | 0.01 | 10.7 | 0.6 | 29.1 | 1.3 | 18.1* | 1.2 |
| | 0.1 | 9.6 | 0.5 | 21.9 | 1.1 | 12.2* | 0.9 |
| | 1.0 | 10.5 | 0.5 | 21.5 | 1.0 | 11.0* | 0.8 |
| | 10.0 | 11.0 | 0.4 | 20.9 | 1.0 | 9.9* | 0.9 |

*p ≦ 0.05 (student's t-test)

As could be shown by comparison (table 2) 2-Cyano-1-[(2-methoxy-6-carboxypyridine-3-yl)-methyl]-aziridine and 2-Cyano-1-[(2-methoxy-6-hydroxymethylpyridine-3-yl)-methyl]-aziridine exhibit a 10 fold higher efficiency than ciamexone.

EXAMPLE 5

Experiments were also performed which showed that the compounds described herein have broader therapeutic action than compounds described in, e.g. U.S. Pat. Nos. 4,321,194, 4,409,236, and 4,410,532. The compounds described in these patents have undesired side-effects when administered at high dosages, in that they induce formation of thermolabile hemoglobin, which in turn provokes formation of "Heinz bodies". These reduce the lifetime of erythrocytes, and lead to hemolytic anemia and splenomogaly.

The following data shows this:

Examination Method

Female mice (balb-c) were administered 500 mg/kg p. a. of a compound as indicated below, dissolved or suspended in a physiological solution of sodium chloride. After 24 hours the animals were bled by cardiac puncture and the amount of thermolabile haemoglobin was determined. For this purpose a haemolysate in sodium phosphate buffer (pH=7.4; 150 mosm, 1% Hb) was prepared from masked erythrocytes. For the determination of the amount of thermolabile haemoglobin the turbidity of an aliquot of the sample before and after incubation (50° C. water bath, 45 min.) was measured photometrically and calculated from the total amount of haemoglobin.

| Compound | Results: thermlabile Hb | Difference | % |
|---|---|---|---|
| control | 6.7 | 0.5 | |
| Ciamexone | 30.2 | 1.1 | 23.5 | 100 |
| A | 8.1 | 0.5 | 1.4 | 6 |
| B | 13.5 | 0.4 | 6.8 | 29 |

Ciamexone: 2-Cyano-1-[(2-methoxy-6-methylpyridin-3-yl)-methyl]-aziridine, i.e., Example 23 of U.S. Pat. No. 4,410,532.

A. 5-[(2-Cyano-1-aziridinyl)methyl]-6-methoxypyridine-2-carboxylic acid (example 1 of this application).

B. 5-[(2-Cyano-1-aziridinyl)methyl]-6-methoxypyridine-2-carboxylaldehyde (example 4 of this application).

As can be seen from the table of results, the inventive compounds induce the formation of thermolabile haemoglobin in a much lower extend than ciamexone (6% and 29% respectively). This was a surprising result.

It will be understood that the specification and examples are illustrative but not limitative of the present invention and that other embodiments within the spirit and scope of the invention will suggest themselves to those skilled in the art.

What is claimed is:

1. A method of regulating an immune response in a patient which comprises administering to the patient an immunomodulating effective amount of an aziridine derivative of the formula:

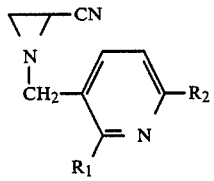

wherein $R_1$ is $C_1$–$C_4$ alkoxy and $R_2$ is hydroxymethyl, carboxyl, alkoxycarbonyl with 2 to 5 carbon atoms, a formyl or carbamoyl or a pharmacologically acceptable salt or a pyridine N-oxide thereof.

2. A method of suppressing an immune response in a patient which comprises administering to the patient an immunosuppressing effective amount of an aziridine derivative of the formula:

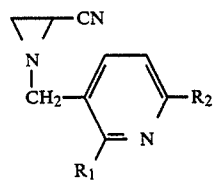

wherein $R_1$ is $C_1$–$C_4$ alkoxy and $R_2$ is hydroxymethyl, carboxyl, alkoxycarbonyl with 2 to 5 carbon atoms, formyl or carbamoyl or a pharmacologically acceptable salt or a pyridine N-oxide thereof.

3. Aziridine derivative compound of the formula:

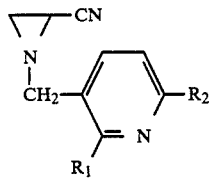

wherein $R_1$ is $C_1$–$C_4$ alkoxy and $R_2$ is hydroxymethyl, carboxyl, alkoxycarbonyl with 2 to 5 carbon atoms, formyl or carbamoyl or a pharmacologically acceptable salt or a pyridine N-oxide thereof.

4. The compound of claim 3 wherein $R_2$ is carboxyl, hydroxymethyl or formyl.

5. The compound of claim 3 wherein $R_1$ is methoxy.

6. The compound of claim 3 designated 2-cyano-1-[(2-methoxy-6-carboxypyridine-3-yl)-methyl]-aziridine.

7. The compound of claim 3 designated 2-cyano-1-[(2-methoxy-6-hydroxymethylpyridine-3-yl)-methyl]-aziridine.

8. The compound of claim 3 designated 2-cyano-1-[(2-methoxy-6-formylpyridine-3-yl)-methyl]-aziridine.

* * * * *